US006350574B1

(12) United States Patent
Montelaro et al.

(10) Patent No.: US 6,350,574 B1
(45) Date of Patent: *Feb. 26, 2002

(54) FLUORESCENCE POLARIZATION—BASED DIAGNOSTIC ASSAY FOR EQUINE INFECTIOUS ANEMIA VIRUS

(76) Inventors: Ronald C. Montelaro, 127 Greenbriar Dr., Wexford, PA (US) 15090; Sarah B. Tencza, 401 Olympia Rd., Pittsburgh, PA (US) 15211; Michael E. Jolley, 34469 N. Circle Dr., Round Lake, IL (US) 60073; Mohammad S. Nasir, 1012 Highgate La., Grayslake, IL (US) 60030

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/400,564

(22) Filed: Sep. 21, 1999

Related U.S. Application Data

(60) Provisional application No. 60/101,553, filed on Sep. 23, 1998.

(51) Int. Cl.[7] .......................... C12Q 1/70; G01N 33/542
(52) U.S. Cl. ............................ 435/5; 435/968; 436/537
(58) Field of Search ...................... 435/5, 968; 436/537

(56) References Cited

U.S. PATENT DOCUMENTS

| 3,932,601 A | 1/1976 | Coggins ....................... 424/12 |
| 4,806,467 A | 2/1989 | Porter et al. .................... 435/7 |
| 5,427,907 A | 6/1995 | Peterson et al. ................ 435/5 |
| 5,976,820 A | 11/1999 | Jolley et al. ................ 435/7.32 |
| 6,110,750 A | 8/2000 | Sugden et al. ............... 436/537 |

OTHER PUBLICATIONS

Chong, Y., et al., "Analysis of Equine Humoral Immune Responses to the Transmembrane Envelope Glycoprotein (gp45) of Equine Infectious Anemia Virus," *Journal of Virology*, vol. 65, No. 2, pp. 1013–1018 (Feb. 1991).
Ball, J., et al., "Detailed Mapping of the Antigenicity of the Surface Unit Glycoprotein of Equine Infectious Anemia Virus by Using Synthetic Peptide Strategies," *Journal of Virology*, vol. 66, No. 2, pp. 732–742 (Feb. 1992).
Chong, Y., et al., "Characterization of the Antigenic Domains of the Major Core Protein (p26) of Equine Infectious Anemia Virus," *Journal of Virology*, vol. 65, No. 2, pp. 1007–1012 (Feb. 1991).
Payne, S., et al., "Localization of Conserved and Variable Antigenic Domains of Equine Infectious Anemia Virus Envelope Glycoproteins Using Recombinant env–Encoded Protein Fragments Produced in *Escheria coli,* " *Virology*, 172:609–615 (1989).

Adamczyk, M., et al., "Estradiol–Mimetic Probes, Preparation of 17alpha–(6–Amino–hexynyl)Estradiol Biotin, Fluorescein and Acridinium Conjugates," *Bioorganic & Medicinal Chemistry Letters*, 8;1281–1284 (1998).
Dandliker, W.B., et al., "Fluorescence Polarization Immunoassay. Theory and Experimental Method," *Immunochemistry*, 10:219–227 (1973).
Kawakami, T., et al., "Nucleotide Sequence Analysis of Equine Infectious Anemia Virus Proviral DNA," *Virology*, 158(2):300–12 (Jun. 1987).
Khanna, P., et al., "4' 5' –Dimethoxy–6–carboxyfluorescein: A Novel Dipole–Dipole Coupled Fluorescence Energy Transfer Acceptor Useful for Fluorescence Immunoassays," *Analytical Biochemistry*, 108:156–161 (1980).
Leroux, C., et al., "Novel and Dynamic Evolution of Equine Infectious Anemia Virus Genomic Quasispecies Associated with Sequential Disease Cycles in an Experimentally Infected Pony," *Journal of Virology*, 71(12):9627–9639 (Dec. 1997).
McGuire, T., "cDNA Sequence of the env Gene of a Pathogenic Equine Infectious Anemia Lentivirus Variant," *Nucleic Acids Research*, 18(1):196 (1990).
Montelaro, R., et al., "Equine Retroviruses," in The Retroviridae, vol. 2, Jay A. Levy, ed., Plenum Press, New York, 1993, pp. 257–360.
Nielsen, K., "A Homogenous Fluorescence Polarization Assay for Detection of Antibody to *Brucella abortus,* " *Journal of Immunological Methods*, 195:161–168 (1996).
Payne, S.L., et al., "Antigenic Variation and Lentivirus Persistence: Variations in Envelope Gene Sequences During EIAV Infection Resemble Changes Reported for Sequential Isolates of HIV," *Virology*, 161:321–331 (1987).
Perry, S.T., et al., "The Surface Envelope Protein Gene Region of Equine Infectious Anemia Virus is Not an Important Determinant of Tropism In Vitro," *Journal of Virology*, 66(7):4085–4097 (Jul. 1992).
Rushlow, K., et al., "Lentivirus Genomic Organization: The Complete Nucleotide Sequence of the env Gene Region of Equine Infectious Anemia Virus," *Virology*, 155:309–321 (1986).
Dandliker, et al., "Application of Fluorescence Polarization to the Antigen–Antibody Reaction," *Immunochemistry*, vol. 1, pp. 165–191, Pergamon Press 1964.

(List continued on next page.)

*Primary Examiner*—Donna C. Wortman
(74) *Attorney, Agent, or Firm*—McDonnell Boehnen Hulbert & Berghoff

(57) ABSTRACT

A fluorescence polarization assay for Equine Infectious Anemia Virus utilizes a short peptide reagent probe derived from a conserved immunodominant region of gp45. The probe is N-terminally labeled, preferably with 6-carboxyfluorescein, and purified by HPLC, which reacts in a homogenous assay with anti-EIAV antibodies contained in the serum of field infected horses and ponies. The assay has a sensitivity of about 90 percent with a specificity approaching 100 percent.

22 Claims, 6 Drawing Sheets

OTHER PUBLICATIONS

Figure 1:
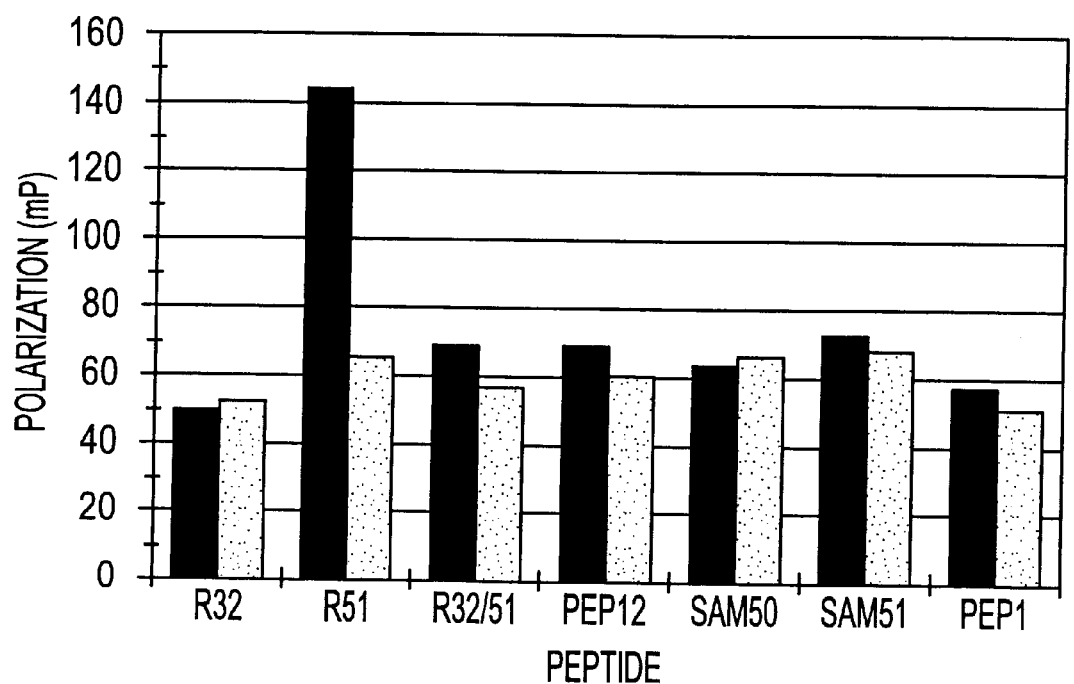

Dandliker, et al., "Quantification of the Antigen–Antibody Reaction by the Polarization of Fluorescence," *Biochemical and Biophysical Research Communications*, vol. 5, No. 4, 1961.

Lin, et al., "Modification of the *Mycobacterium Bovis* Extracellular Protein MPB70 with Flurescein for Rapid Detection of Specific Serum Antibodies by Fluorescence Poloarization," *Clinical and Diagnostic Laboratory Immunology,* vol. 3, No. 4, Jul. 1996, pp. 438–443.

Nasir, et al., "Fluorescence Polarization: An Analytical Tool for Immunoassay and Drug Discovery," *Combinatorial Chemistry & High Throughput Screening,* vol. 2, pp. 177–190, (1999).

SEQUENCE LISTING

<160> NUMBER OF SEQ ID NOS: 21

<210> SEQ ID NO 1
<211> LENGTH: 14
<212> TYPE: PRT
<213> ORGANISM: Equine infectious anemia virus

<400> SEQUENCE: 1

Ile Gly Cys Ile Glu Arg Thr His Val Phe Cys His Thr Gly
1               5                   10

<210> SEQ ID NO 2

```
<211> LENGTH: 13
<212> TYPE: PRT
<213> ORGANISM: Equine infectious anemia virus

<400> SEQUENCE: 2

Gly Cys Ile Glu Arg Thr His Val Phe Cys His Thr Gly
1               5                   10

<210> SEQ ID NO 3
<211> LENGTH: 12
<212> TYPE: PRT
<213> ORGANISM: Equine infectious anemia virus

<400> SEQUENCE: 3

Cys Ile Glu Arg Thr His Val Phe Cys His Thr Gly
1               5                   10

<210> SEQ ID NO 4
<211> LENGTH: 15
<212> TYPE: PRT
<213> ORGANISM: Equine infectious anemia virus

<400> SEQUENCE: 4

Leu Ile Gly Cys Ile Glu Arg Thr His Val Phe Cys His Thr Gly
1               5                   10                  15

<210> SEQ ID NO 5
<211> LENGTH: 9
<212> TYPE: PRT
<213> ORGANISM: Equine infectious anemia virus

<400> SEQUENCE: 5

Cys Ile Glu Arg Thr His Val Phe Cys
1               5

<210> SEQ ID NO 6
<211> LENGTH: 13
<212> TYPE: PRT
<213> ORGANISM: Equine infectious anemia virus

<400> SEQUENCE: 6

Lys Glu Arg Gln Gln Val Glu Glu Thr Phe Asn Leu Ile
1               5                   10

<210> SEQ ID NO 7
<211> LENGTH: 12
<212> TYPE: PRT
<213> ORGANISM: Equine infectious anemia virus

<400> SEQUENCE: 7

Glu Arg Gln Gln Val Glu Glu Thr Phe Asn Leu Ile
1               5                   10

<210> SEQ ID NO 8
<211> LENGTH: 11
<212> TYPE: PRT
<213> ORGANISM: Equine infectious anemia virus

<400> SEQUENCE: 8

Arg Gln Gln Val Glu Glu Thr Phe Asn Leu Ile
1               5                   10

<210> SEQ ID NO 9
<211> LENGTH: 10
<212> TYPE: PRT
```

<213> ORGANISM: Equine infectious anemia virus

<400> SEQUENCE: 9

Gln Gln Val Glu Glu Thr Phe Asn Leu Ile
1               5                   10

<210> SEQ ID NO 10
<211> LENGTH: 9
<212> TYPE: PRT
<213> ORGANISM: Equine infectious anemia virus

<400> SEQUENCE: 10

Gln Val Glu Glu Thr Phe Asn Leu Ile
1               5

<210> SEQ ID NO 11
<211> LENGTH: 8
<212> TYPE: PRT
<213> ORGANISM: Equine infectious anemia virus

<400> SEQUENCE: 11

Val Glu Glu Thr Phe Asn Leu Ile
1               5

<210> SEQ ID NO 12
<211> LENGTH: 7
<212> TYPE: PRT
<213> ORGANISM: Equine infectious anemia virus

<400> SEQUENCE: 12

Glu Glu Thr Phe Asn Leu Ile
1               5

<210> SEQ ID NO 13
<211> LENGTH: 27
<212> TYPE: PRT
<213> ORGANISM: Equine infectious anemia virus

<400> SEQUENCE: 13

Lys Glu Arg Gln Gln Val Glu Glu Thr Phe Asn Leu Ile Ile Gly Cys
1               5                   10                  15

Ile Glu Arg Thr His Val Phe Cys His Thr Gly
            20                  25

<210> SEQ ID NO 14
<211> LENGTH: 26
<212> TYPE: PRT
<213> ORGANISM: Equine infectious anemia virus

<400> SEQUENCE: 14

Ala Asp Asp Trp Asp Asn Arg His Pro Leu Pro Asn Ala Pro Leu Val
1               5                   10                  15

Ala Pro Pro Gln Gly Pro Ile Pro Met Thr
            20                  25

<210> SEQ ID NO 15
<211> LENGTH: 19
<212> TYPE: PRT
<213> ORGANISM: Equine infectious anemia virus

<400> SEQUENCE: 15

His Pro Leu Pro Asn Ala Pro Leu Val Ala Pro Pro Gln Gly Pro Ile
1               5                   10                  15

```
Pro Met Thr

<210> SEQ ID NO 16
<211> LENGTH: 14
<212> TYPE: PRT
<213> ORGANISM: Equine infectious anemia virus

<400> SEQUENCE: 16

Ala Pro Leu Val Ala Pro Pro Gln Gly Pro Ile Pro Met Thr
 1               5                  10

<210> SEQ ID NO 17
<211> LENGTH: 32
<212> TYPE: PRT
<213> ORGANISM: Equine infectious anemia virus

<400> SEQUENCE: 17

Val Asp Cys Thr Ser Glu Glu Met Asn Ala Phe Leu Asp Val Val Pro
 1               5                  10                  15

Gly Gln Ala Gly Gln Lys Gln Ile Leu Leu Asp Ala Ile Asp Lys Ile
                20                  25                  30

<210> SEQ ID NO 18
<211> LENGTH: 25
<212> TYPE: PRT
<213> ORGANISM: Equine infectious anemia virus

<400> SEQUENCE: 18

Leu Glu Thr Trp Lys Leu Val Lys Thr Ser Gly Val Thr Pro Leu Pro
 1               5                  10                  15

Ile Ser Ser Glu Ala Asn Thr Gly Leu
                20                  25

<210> SEQ ID NO 19
<211> LENGTH: 16
<212> TYPE: PRT
<213> ORGANISM: Equine infectious anemia virus

<400> SEQUENCE: 19

Ser Gly Val Thr Pro Leu Pro Ile Ser Ser Glu Ala Asn Thr Gly Leu
 1               5                  10                  15

<210> SEQ ID NO 20
<211> LENGTH: 10
<212> TYPE: PRT
<213> ORGANISM: Equine infectious anemia virus

<400> SEQUENCE: 20

Pro Ile Ser Ser Glu Ala Asn Thr Gly Leu
 1               5                  10

<210> SEQ ID NO 21
<211> LENGTH: 20
<212> TYPE: PRT
<213> ORGANISM: Equine infectious anemia virus

<400> SEQUENCE: 21

Tyr Gly Gly Ile Pro Gly Gly Ile Ser Thr Pro Ile Thr Gln Gln Ser
 1               5                  10                  15

Glu Lys Ser Lys
                20
```

FLUORESCENCE POLARIZATION— BASED DIAGNOSTIC ASSAY FOR EQUINE INFECTIOUS ANEMIA VIRUS

CROSS-REFERENCE TO RELATED APPLICATIONS

This application claims the benefit of U.S. Provisional Application No. 60/101,553, filed on Sep. 23, 1998.

BACKGROUND OF THE INVENTION

1. Field of the Invention

This invention is related to the field of veterinary diagnostics and, more particularly, to a homogeneous fluorescence polarization-based assay to detect specific antibodies contained in the blood of horses and ponies infected with the lentivirus, aetiologic for Equine Infectious Anemia (EIA).

2. Description of Related Art

Equine Infectious Anemia Virus (EIAV) is a lentivirus genetically related to human immunodeficiency virus type 1 (HIV-1) that infects horses, ponies, and other equids (for a recent review see Montelaro, et al., "Equine Retroviruses, in J. A. Levy, Ed., The Retroviridae, Vol. 2, p. 257 (Plenum Press: 1993 N.Y.). It causes a chronic disease characterized by a period of cyclic fevers and viremia, followed by clinical quiescence. The animals generally survive this disease but remain infected, becoming lifelong inapparent carriers; they appear to be healthy but in fact still may have virus in their blood There are thousands of EIAV-positive horses in the US; most of them reside in the "hot zone", a group of 18 states along the Gulf coast and Mississippi valley (see Cordes, "Equine Infectious Anemia", USDA 91-55-032 (1996). The disease is most prevalent there due to the humid environment that favors growth of horse flies, the major vector of transmission of EIAV. In an attempt to control the spread of this virus, horses are tested before showing, breeding, or crossing state lines. If a horse is found to be seropositive, its movement is severely restricted; the horse must be euthanized or quarantined with a 200-yard barrier for the rest of its life. However, because testing is not yet mandatory for all horses, it is estimated that over 80% have never been tested; this pool of horses may be a major reservoir for the virus. Efforts are underway to encourage, and in some states mandate, testing of all equids to better control this disease and reduce the rate of infection.

EIAV-infected animals mount a vigorous immune response to the viral infection. This results in reduction of viremia during clinical quiescence to very low, often undetectable, levels. This immune response is characterized by high-titer antibodies directed to three major viral antigens: the envelope glycoproteins, gp90 and gp45, and the capsid protein or core antigen, p26. Due to the presence of high levels of antibody and low levels of virus during most of the disease course, diagnostic assays have focused on detection of viral antibodies.

One way to improve testing compliance is to develop better, faster assays. Current official diagnostic assays for EIAV include agar gel immunodiffusion (AGID) as reported in Coggins, et al., Cornell Vet USA LX: 330 (1970), competitive ELISA (C-ELISA), and synthetic antigen ELISA (SA-ELISA). The first two assays detect antibodies to the major core protein p26, which has a well conserved structure but is a relatively poor immunogen compared to the envelope proteins, gp90 and gp45. SA-ELISA detects antibodies to gp45 and is approved for use, but can have a lower sensitivity. The major drawbacks of the AGID test are the length of time it takes to test the samples and the technical difficulty in interpreting the results. ELISA-based tests can be completed in several hours, but in a recent study the C-ELISA had a 2% false positive rate, as reported in Issel, EIA-Hotzone Project, U of Kentucky.

Fluorescence polarization (FP) has been used as a tool to monitor protein-protein, protein-peptide; and other intermolecular interactions, as described in Jolley, J. Biomol, Screen 1: 33 (1996). First described by Perrin (1926), it is the property of many fluorophores that they emit light in the same direction in which it is absorbed. When a fluorophore is freely rotating in solution, the light is emitted in all directions by virtue of the molecule's rotation during the lifetime of the fluorescence emission; it is non-polarized. If, however, the fluorophore is part of a slowly rotating molecule (one that is large or in a viscous environment), the molecule does not rotate quickly with respect to the lifetime of the fluorescence, and the emission will occur in roughly the same direction as the absorption; it is polarized. This property of fluorescence can therefore be used to distinguish small molecules (e.g. fluorescent-labeled peptides) from large ones (e.g. peptide bound to antibody). Relatively recent advances in instrumentation have allowed the use of this phenomenon to develop rapid immunoassays; for a large number of analytes including therapeutic drugs and metabolites as well as antibodies to infectious agents as, for example, Nielsen, et al., J. Immunol. Methods 195: 161 (1996). These assays can be performed in a matter of minutes (vs. hours or days for the other tests) and usually do not require extensive sample preparation. In addition, the materials required for the assay are relatively simple and highly stable, making this technique attractive for field use.

In light of the need for a more rapid assay that can be used in the field to detect EIAV-infected horses, we pursued FP as a medium on which to develop a new diagnostic for anti-EIAV antibodies. We selected, labeled, and evaluated several candidate peptides for their ability to detect the presence of antibodies to three EIAV proteins. This investigation has led to the development of an FP-based assay which uses a well-conserved, immunodominant region of gp45 transmembrane protein. The test is rapid and possesses both high sensitivity and very high specificity. It reacts with antibodies in serum or plasma from both experimentally- and field-infected animals from various geographic areas.

SUMMARY OF THE INVENTION

In a first principal aspect, the present invention provides a synthetic antigen probe comprising a fluorophore conjugated to a peptide comprising a sequence of amino acids selected from the group consisting of SEQ ID NO:1, SEQ ID NO:2, SEQ ID NO:3, SEQ ID NO:4, and SEQ ID NO:5, wherein the synthetic fluorescent antigen probe binds to serum antibodies to equine infectious anemia virus to produce a detectable change in fluorescence polarization.

In a second principal aspect, the present invention provides an assay for serum antibodies reactive to an antigen common to a number of field strains of equine infectious anemia virus that comprises the following steps. First, a serum specimen suspected of containing antibodies reactive with an antigen of equine infectious anemia virus is diluted with a buffer solution to provide a buffered specimen. Next, a synthetic fluorescent antigen probe is added to the buffered specimen. The synthetic fluorescent antigen probe comprises a fluorophore conjugated to a peptide comprising an amino acid sequence selected from the group consisting of SEQ ID NO:1, SEQ ID NO:2, SEQ ID NO:3, SEQ ID NO:4, and SEQ ID NO:5. The buffered specimen with added antigen probe is incubated for a time sufficient to permit binding in solution of the EIAV antibodies with the antigen probe to provide a reaction product. The fluorescence polarization of the reaction product is then compared to a blank control.

In a third principal aspect, the present invention provides a diagnostic assay kit for detecting serum antibodies reactive to a number of field strains of equine infectious anemia virus. The kit is comprised of a synthetic fluorescent antigen probe in amount suitable for at least one assay and suitable packaging. The synthetic fluorescent antigen probe comprises a fluorophore conjugated to a peptide comprising a sequence of amino acid selected from the group consisting of SEQ ID NO:1, SEQ ID NO:2, SEQ ID NO:3, SEQ ID NO:4, and SEQ ID NO:5.

In accordance with preferred embodiments of the present invention, the fluorescence polarization-based diagnostic assay, utilizing a synthetic fluorescent antigen probe, is rapid, easy to use, and has a high sensitivity to and specificity for a number of field strains of equine infectious anemia virus.

BRIEF DESCRIPTION OF THE DRAWINGS

FIG. 1 shows the reactivity of the original panel of peptides with anti-EIAV IgG.

FIG. 2 shows the influence of peptide length and fluorescein linkage on FP reactivity of peptide R51.

FIG. 3 shows the influence of the peptide length on FP reactivity of peptide R32.

FIG. 4 shows the reactivity of R51-6CF with field-infected and uninfected sera.

FIG. 5 shows relative peptide reactivity measured by antifluorescein-capture ELISA.

FIG. 6 shows early three-week detection of newly sero-converted animals.

DETAILED DESCRIPTION OF THE PREFERRED EMBODIMENT

The initial panel comprised seven peptides, each derived from one of the three major proteins of EIAV: peptide 1 and peptide 12 from gp90 (surface unit), R51, R32 and R51/32 from gp45 (transmembrane), and Sam50 and Sam51 from p26 (capsid). Candidate peptides were chosen based on previous work showing regions of broadly reactive antigenicity in certain proteins of EIAV, namely, the p26 capsid, as described in Chong et al., J. Virology, 65: 1007 (1991), the gp45 transmembrane, as described in Chong, et al., J. Virology, 65: 1013 (1991), and the gp90 surface unit, as described in Ball, et al., J. Virology, 66: 732 (1992).

Table 1 lists these peptides and cross-references the peptide name with the SEQ. ID. NO., the amino acid sequence, and the source protein. These sequences were based on the Prototype (cell-adapted Wyoming) strain of EIAV, described in Rushlow, et al., Virology, 155: 309 (1986), and correspond to conserved regions of the envelope proteins, as shown in Payne, et al., Virology, 172: 606 (1989).

TABLE 1

Summary of EIAV Diagnostic peptides

| Peptide Name | SEQ ID NO | Sequence | Source |
|---|---|---|---|
| R51 | 1 | IGCIERTHVFCHTG | gp45 (env 534–547) |
| R51G | 2 | GCIERTHVFCHTG | gp45 (env 535–547) |
| R51C | 3 | CIERTHVFCHTG | gp45 (env 536–547) |
| R51L | 4 | LIGCIERTHVFCHTG | gp45 (env 533–547) |
| R51CysCys | 5 | CIERTHVFC | gp45 (env 536–544) |
| R32 | 6 | KERQQVEETFNLI | gp45 (env 522–534) |
| R32ER | 7 | ERQQVEETFNLI | gp45 (env 523–534) |
| R32R | 8 | RQQVEETFNLI | gp45 (env 524–534) |
| R32QQ | 9 | QQVEETFNLI | gp45 (env 525–534) |
| R32Q | 10 | QVEETFNLI | gp45 (env 526–534) |
| R32V | 11 | VEETFNLI | gp45 (env 527–534) |
| R32E | 12 | EETFNLI | gp45 (env 528–534) |
| R32/51 | 13 | KERQQVEETFNLIIGCIERTHVFCHTG | gp45 (env 522–547) |
| Sam50 | 14 | ADDWDNRHPLPNAPLVAPPQGPIPMT | p26 (170–201) |
| Sam50H | 15 | HPLPNAPLVAPPQGPIPMT | p26 (177–201) |
| Sam50A | 16 | APLVAPPQGPIPMT | p26 (182–201) |
| Sam51 | 17 | VDCTSEEMNAFLDVVPGQAGQKQILLDAIDKI | p26 (202–227) |
| Peptide 12 | 18 | LETWKLVKTSGVTPLPISSEANTGL | gp90 (env 408–434) |
| Pep12S | 19 | SGVTPLPISSEANTGL | gp90 (env 419–434) |
| Pep12 | 20 | PISSEANTGL | gp90 (env 425–434) |
| Peptide1 | 21 | YGGIPGGISTPITQQSEKSK | gp90 (env 1–20) |

Probes based on all three proteins were explored because whereas p26 is more conserved among EIAV strains, the level of antibody induced is 10-to-100-fold lower to this protein compared to the envelope proteins, gp90 and gp45. The peptides correspond to conserved regions of the proteins that have been shown to react broadly with equine sera in an ELISA-based format.

Due to problems encountered with testing horse serum, the initial evaluation made use of purified IgG from a reference long-term, field-infected horse (Lady). Purified IgG from field infected horse serum (100 $\mu$g/ml) was incubated with the candidate probe peptides (2 nM) in PBS for 20 min. The results are shown in FIG. 1, wherein black bars indicate probe added to IgG and gray bars indicate probe in buffer alone. All peptides were the 5-carboxyfluorescein derivatives. Most of the peptides were found to be insensitive to the presence of 60–100 $\mu$g/ml Lady IgG in PBS; however R51-5CF, derived from gp45, did undergo an increase in FP in the presence of Lady IgG (see FIG. 1) from a free-peptide polarization level of about 60 mP to around 140 MP. The other peptides in the panel had only slight changes in polarization in the presence of Lady IgG. Based on these results, we used R51-5CF to explore the proper buffer conditions for interaction with antibodies in whole serum.

It was observed that phosphate-buffered saline (10 mM Na, K phosphate, 150 mM NaCl, pH 7.4) with Tween 20, Triton X-100, or lithium dodecyl sulfate often caused precipitation of serum proteins and resulted in low, and occasionally even negative, polarization values due to severe background intensities and low lamp feedback. Several different buffer compositions and detergents were therefore tested for compatibility with horse serum. When horse serum was diluted 1:50 or 1:100 into 20–50 mM sodium phosphate without NaCl, this problem was virtually eliminated. Low salt conditions also obviated the need for a detergent in the buffer, although signal-to-noise ratios were slightly improved when 0.05% Tween-20 was added to the buffer. Under the low-salt conditions, the polarization of peptide R51-5CF increased from 50 mP to over 200 mP with a 1:100 dilution of a strong positive EIAV antiserum from an experimental infection (Pony 95). Thus it was determined that the optimal buffer composition for the FP assay was 50 mM sodium phosphate, pH 6.8–7.0.

EXAMPLE 1

General Methods

Horse Sera. Serum from EIAV field-infected and uninfected horses were generous gifts from the Texas Animal Health Commission, Missouri Department of Agriculture, and University of Kentucky (Utah, Florida, and Oklahoma field-infected sera). Prior to use and after a freeze-thaw cycle, the sera were centrifuged at 12000×g for 2 minutes to pellet any precipitated protein.

Peptide Synthesis and Labeling. Peptides were produced on a 0.2-mmol scale using a Millipore Automated Peptide Synthesizer and standard Fmoc chemistry, as described previously in Fontenot, et al., Peptide Res., 4: 19 (1991). Peptides were labeled with 5-or 6-carboxyfluorescein (Molecular Probes, Eugene, OR) while still on the resin, thus placing the fluorophore on the N-terminus of the peptide. The Fmoc protecting group was removed from the N-terminus of the peptide-resin by 25% piperidine in dimethylformamide (DMF) followed by four washes with DMF. The fluorescent probe was dissolved in DMF to a concentration of 0.3 M and this solution was mixed with 0.9 M DIPEA and 0.6 M HOBT/TBTU in a 5:4:2 ratio. The dye mixture was added to the resin and incubated overnight with shaking. Following four washes, each with DMF and dichloromethane, the resin was dried under vacuum. The dye-conjugated peptides were cleaved from the resin using standard TFA cleavage procedures followed by multiple ether extractions. Peptides were purified by reverse-phase HPLC and analyzed by mass spectrometry to confirm that the desired product was obtained.

Anti-Fluorescein Capture ELISA. In order to measure antibody binding to test peptides without regard to their suitability for FP, an anti-fluorescein capture ELISA was used. To each well of an Immulon 2 HB 96-well plate (Dynex, Chantilly Va.) was added 50 µL rabbit anti-fluorescein antibody (Molecular Probes), 3.5 g/ml in 50 mM sodium bicarbonate, pH 9.6; the plates were sealed and incubated overnight. The wells were blocked with Blotto (5% nonfat dry milk, 5% normal bovine serum, 0.025% Tween 20 in PBS (PBST). The plates were then incubated with test horse sera, diluted 1:100 in Blotto, for 1 h at RT, washed as above, then incubated with anti-horse IgG(Fc)-HRP (United States Biochemical), diluted 1:10$_5$ in Blotto, for 1 h at RT and washed. The substrate, TM Blue Soluble reagent (200 µL/well; Intergen, Milford Mass.) was added and incubated for 20 minutes with shaking, and the reaction stopped with the addition of 50 µL/well 1.0 N $H_2SO_4$ for 5 minutes with shaking. Absorbance at 450 nm was measured on a Dynex MR5000 microplate reader. Because each peptide caused a slightly different background absorbance, control wells containing no horse serum were included for each peptide tested.

Fluorescence Polarization (FP) Measurements. The fluorescein-labeled peptides were evaluated for their suitability as probes for FP using an FPM-1 Fluorescence Polarization Analyzer (Jolley Consulting and Research, Grayslake Ill.) batch mode with the following settings: PMT gain 80, heater off, single read. Serum was diluted 1:100 or 1:50 into 2 mL of buffer in 12×75 mm borosilicate glass tubes (VWR). After reading the blank, fluorescently labeled peptide was added to a final concentration of 1–2 nM (100K–200K total intensity) and incubated for at least 15 minutes. The FP of the sample was measured and expressed as millipolarization units (mP). Some of the sera were very dark, presumably due to hemolysis. If such a serum sample had low lamp feedback (<0.63), a two-fold further dilution was tested. Polarization data was output to a computer running the FPM-1 data collection software, then converted to an ASCII text file and imported into the Quattro Pro spreadsheet program (Corel, Ottawa, Ontario) for data analysis and graphing.

EXAMPLE 2

Once serum testing was enabled, we tested the panel of peptides with sera from both experimentally and field-infected horses. Although some reactivity was observed with peptides R32 and peptide 12 against Pony 95, R51-5CF again was the only peptide from the original panel that was sensitive to serum from field infected horses. This result was in contrast to our ELISA results, in which these two peptides reacted very strongly with both Pony 95 and Lady sera. Thus, ELISA reactivity was not a good predictor of FP reactivity. None of the peptides reacted with EIAV-negative horse serum in either the FP or ELISA assays.

Figure 2:
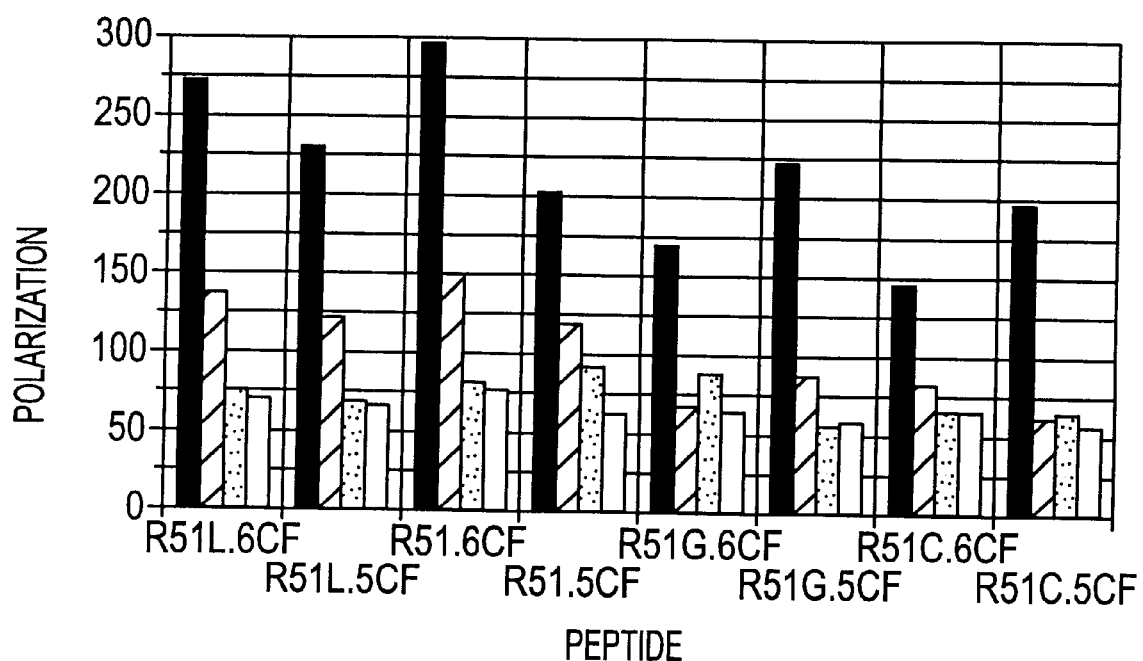

Based on these data the R51 peptide was optimized for maximum FP signal by exploring the effects of alterations in peptide length and fluorescein linkage. Because different fluorescein linkages can result in differences in sensitivity in the FP assay, R51 peptide was labeled with 6-carboxyfluorescein so the difference between the two labels could be ascertained. Analogs of R51 were also synthesized possessing 0–3 amino acid residues between the N-terminal cysteine and the fluorescein probe. Peptides (approx. 2 nM) were incubated with a 1:100 dilution of serum in 50 mM sodium phosphate, pH 6.8, for 20 minutes. The results are shown in FIG. 2, in order of decreasing peptide length. In FIG. 2, black bars show the results for experimentally-infected (pony 95), hatched bars for field infected (Lady), gray bars for uninfected (Petite), and white bars for no serum added. It was found that neither reducing nor increasing peptide length improved signal but changing from a 5- to 6-carboxyfluorescein label did significantly improve the signal of R51 with positive sera (220 mP for 5CF vs.>300 for 6CF) without increasing background as shown in FIG. 2. As the R51-6CF probe was the most sensitive to the positive sera tested, 6-carboxyfluorescein is the preferred fluorophore. However, other fluorophores, such as rhodamine, BODIPY™, Texas Red™ and Lucifer yellow, could also be used. For a detailed listing of a variety of commercially available fluorophores, see *Handbook of Fluorescent Probes and Research Chemicals*, ed. Karen Larison, by Richard P. Haughland, Ph.D., 5th ed., 1992, published by Molecular Probes, Inc.

Because R51 contains two Cys residues that may form a loop in the native protein, the differences in reactivity were assessed between linear or cyclized peptide (cyclic by virtue of an intramolecular disulfide bond). In particular, the cyclized peptide was more sensitive to field isolates than the linear form of the probe. However, the probe was prone to precipitation under conditions that allow cyclization, which caused an increase in the polarization of the free probe and reduction of sensitivity; therefore, the peptide stock solutions contained dithiothreitol (DTT) to prevent aggregation. The peptide was found to be stable upon dilution, and probably spontaneously cyclizes under those conditions.

Because of the loop formed by the two Cys residues in R51, it is believed that the sequence of amino acids between and including the two Cys residues, i.e., the R51CysCys peptide, SEQ. ID. NO:5 (see Table 1), constitutes the minimum peptide length useful for detecting serum antibodies in field-infected equines. The maximum useable peptide length is not known. However, other experimental work has shown that peptides as large as 50 amino acids in length, that include the R51 peptide, have been found to react to such serum antibodies.

EXAMPLE 3

Figure 3:
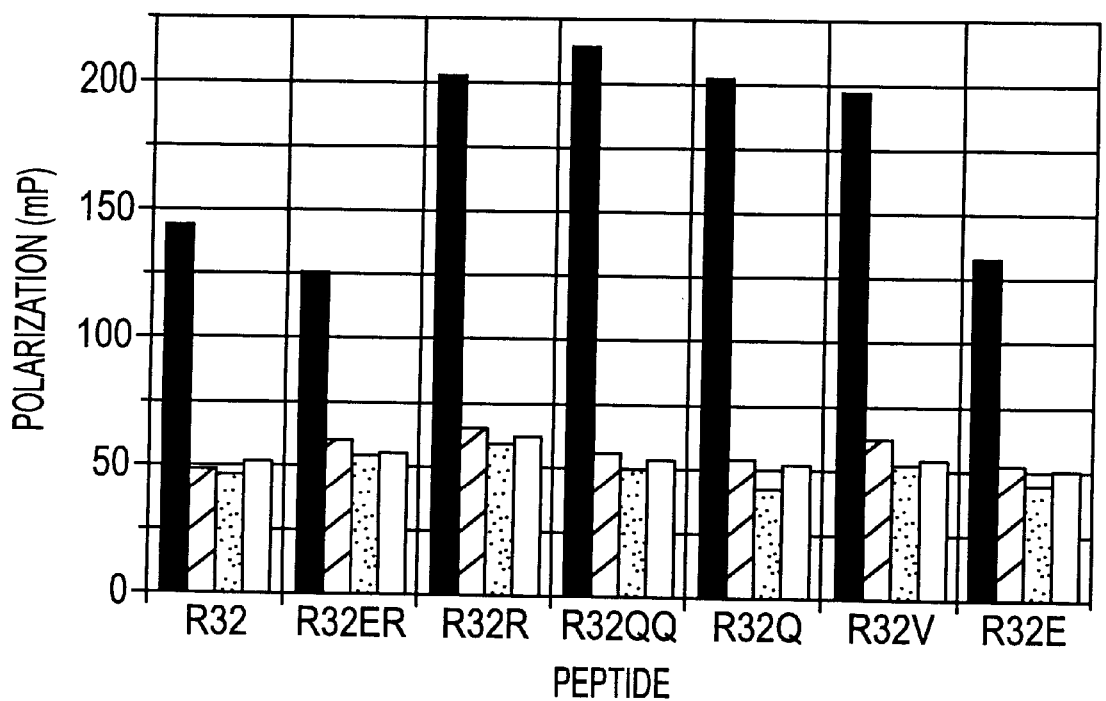

In addition to R51, peptides R32 and pep12 were engineered in an effort to improve their sensitivity in FP. These peptides showed strong and broad reactivity in the antifluorescein ELISA, but did not exhibit an increase in FP upon mixing with purified antibodies from a field-infected animal. A series of peptides of different lengths was synthesized and labeled at their N-terminal by fluorescein-6-isothiocyanate. The complete R32 series was tested for reactivity to positive and negative sera as set forth in FIG. 3. We observed a bell-shaped curve, with a maximum FP of >200 mP with a 1:100 dilution of pony 95. The most sensitive peptide was R32QQ, a 10-amino acid peptide. The R32 peptides all showed good reactivity with strongly positive experimentally infected animals (pony 95, for example) but little reactivity with serum from the field-infected horse (Lady). Likewise, neither of the pep12 analogs displayed a large change in FP in the presence of Lady serum (data not shown). Therefore, it was concluded that under the conditions of the assay, these peptides are sensitive only to experimentally infected horse sera and are not appropriate for a diagnostic assay for field infected equids.

EXAMPLE 4

Figure 4:
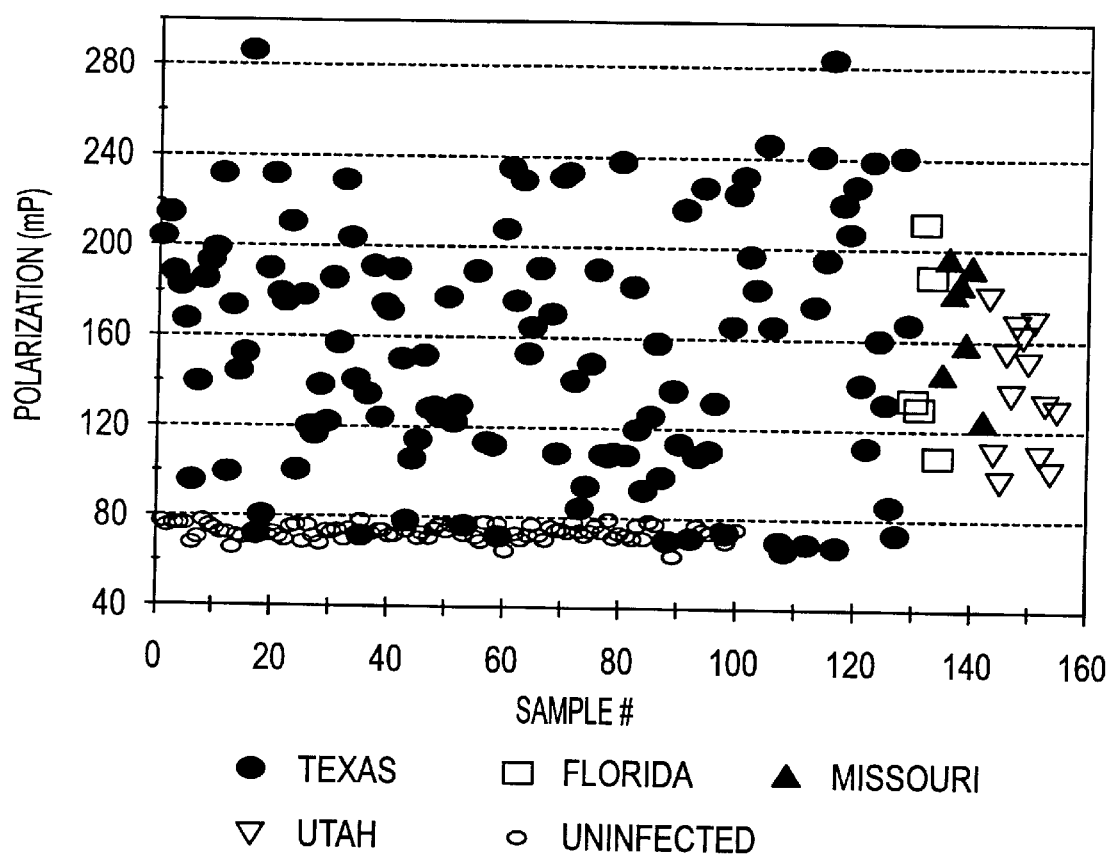

Focusing on our highly sensitive probe, R51-6CF, 258 sera from both uninfected and field infected horses from Texas, Missouri, Utah, and Florida were tested. The specificity of the probe was examined by testing serum samples that were negative by AGID (FIG. 4, open circles). Testing at a 1:100 dilution, the 110 negative serum samples had very low and consistent polarization values (73.6±3.0 mP), indicating that specificity was very high for R51-6CF. Out of the 110 negative samples tested, only two initially reacted in the assay, and both of these had signs of bacterial contamination. Upon sterile filtration and re-testing, these two samples gave consistently negative readings. Thus provided that the samples were kept in good condition our assay had a specificity of 100%. This represents a practically perfect correlation with a negative AGID result and is an improvement in specificity over the C-ELISA. In addition to the high specificity, the polarization values were so consistent that one could distinguish a positive from a negative sample by as few as 5 mP units.

In order to determine the sensitivity of this assay, 153 sera from field-infected animals were tested at a 1:100 dilution. These sera were obtained from geographically distinct regions throughout the United States: Texas, Utah, Missouri, and Florida. The probe reacted well with most of the sera: the distribution of values is represented in FIG. 4, showing the results for peptide (~2nM) incubated with a 1:100 dilution of sera from field-infected horses. Sera are grouped by geographic region. The measurable sera caused the polarization of R51-6CF to increase to an average mP value of 150±55, a clear and significant difference from the average of the negative sera. The probe reacts well with antibodies from diverse geographic regions, indicating that the epitope is well conserved and is thus suitable for a diagnostic antigen. The overall percent reactivity of this serum panel in the FP assay was found to be 93%. This represents the correlation between reactivity in the two assay formats; actual percent sensitivity to true positives may need to be determined by Western blotting of the discrepant samples. In two other studies, the average sensitivity of the FP assay was 95% and the specificity was 100%.

EXAMPLE 5

Some of the sera from Missouri (4/10) could not be tested due to interference from a high level of hemolysis, resulting in low lamp feedback values. However, we found 14 samples out of 123 positive Texas sera that did not react with this probe in the FP assay (FIG. 4), even at a 1:50 dilution. In order to confirm the serological status of FP-unreactive sera, they were tested in a western blot (data not shown) as well as in the antifluorescein-capture ELISA using the seven original peptides derived from the three major antigens mentioned above (FIG. 5). Sera (1:50 dilution) were tested for reactivity to four EIAV-derived, fluorescein-labeled peptides in an ELISA format as described in the methods. NHS, normal (uninfected) horse serum; Tx43 through Tx117, FP-nonreactive, Tx47 through pony 95, FP-reactive sera. Black bars, peptide R51F; hatched bars, R32; gray bars, pep12; white bars, Sam50. These data indicated that several of the FP-nonreactors have no measurable antibody to either R51 or R32 in the ELISA format, and bind only weakly to the other peptides (pep12 from gp90 and Sam50 from p26). Thus these sera do not appear to have antibody to the gp45 antigen.

Figure 5:
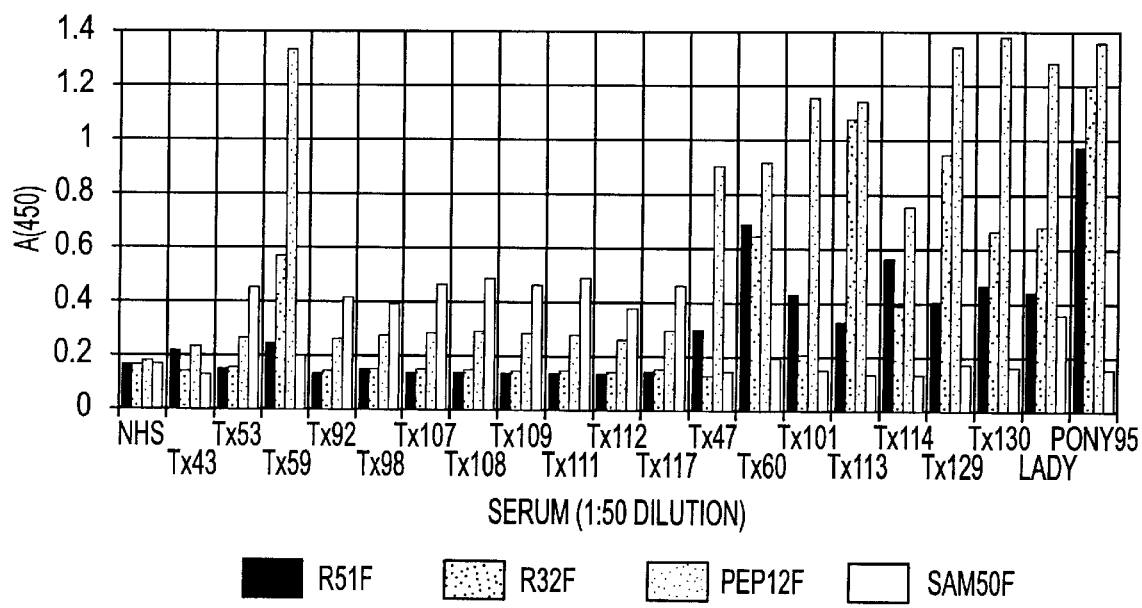

Of the samples that were non-reactive in FP but confirmed to be positive, several exhibited ELISA reactivity to the p26-derived Sam50 peptide that was higher than some of the positive controls (FIG. 5). These data suggested that although the original Sam50 peptide was insensitive to EIAV-positive sera, a shorter form of the Sam50 peptide might be more sensitive in the FP assay for these serum samples. Two shortened analogs of Sam50; Sam50A, a 14-AA peptide, and Sam50H, a 19-AA peptide, were synthesized. However when tested in the FP assay, none of these analogs displayed a measurable interaction with the EIAV-positive sera. This lack of reactivity may be due to the low levels of antibodies to this epitope and/or that the peptide is still too long for the fluorophore to undergo a change in polarization upon antibody binding. Further testing will be needed to determine whether a Sam50-based peptide will be able to detect antibodies to EIAV when the R51-6CF peptide does not react.

EXAMPLE 6

Figure 6:
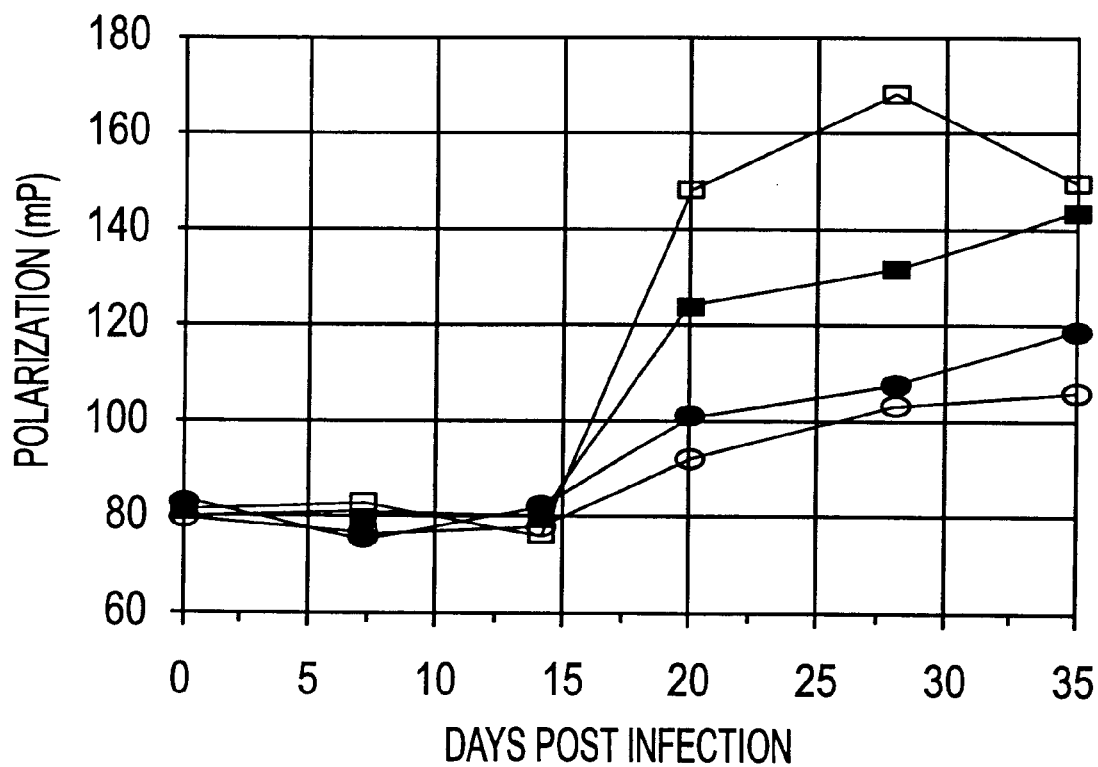

In addition to testing sera from various geographic areas, the ability of R51-6CF to detect antibodies early in infection was examined. Serum samples acquired weekly during an experimental infection of four ponies were tested for the presence of anti-EIAV antibodies by FP. This assay detected antibody in both 1:100 and 1:50 dilutions of serum at 3 weeks post infection (FIG. 6), which is the same time at which antibody was first detected by Con A capture ELISA (Hammond et al., J. Virology 71: 3840 (1997)). These data indicate that the FP assay is at least as sensitive as an ELISA is in detecting early antibody responses to EIAV infection. In addition, the test was as or more sensitive than AGID in detecting early antibody responses; ponies 561, 562, and 564 were AGID positive on day 21, and pony 567 was not positive until day 23. Thus the FP technique may have an advantage over AGID in the detection of early immune responses; this may be due to the fact that the immune response to envelope tends to arise earlier and to higher levels than do the antibodies to p26. In summary, peptides derived from all three of these proteins were evaluated and found that R51, the peptide derived from gp45, had the best combination of high reactivity and broad specificity, as it was able to detect antibodies from horses infected with many field strains. The R51 peptide is based on a region that is immunodominant in lentiviruses, yet is well conserved. Although the amino acid sequences of envelope proteins of lentiviruses generally vary more than the capsid and other core proteins, it was found that antigenic variation was not a large problem in this case, since we have achieved approximately 90% sensitivity with a single envelope-based peptide antigen. The few samples that did not bind to this probe may be from animals infected with an unusual strain of EIAV that bears sequence variation in this region of the protein. For these few sera, a peptide based on p26 or gp90 may need to be developed. The R51 non-reactor ponies did show some reactivity to Sam50 in the peptide ELISA. The R51 nonreactive horses do show antibody reactivity to all three major proteins in a Western blot, so efforts are underway to find a peptide epitope that will react with these field infected sera.

Assay Kit

The synthetic fluorescent antigen probe of the present invention is preferably made available in kit form. The kit includes a quantity of buffer solution for diluting serum specimens suspected of containing antibodies to EIAV, the synthetic fluorescent antigen probe in amount suitable for at least one assay (i.e., about 100 nanograms), along with suitable packaging and instructions for use. The synthetic fluorescent antigen probe may be provided in solution, as a liquid dispersion, or as a substantially dry powder (e.g., in lyophilized form).

The suitable packaging can be any solid matrix or material, such as glass, plastic, paper, foil, and the like, capable of separately holding within fixed limits the buffer and the synthetic fluorescent antigen probe. For example, the buffer solution and the synthetic fluorescent antigen probe may be provided in separate labeled bottles or vials made of glass or plastic.

The synthetic fluorescent antigen probe comprises a peptide comprising a sequence of amino acids selected from the group consisting of SEQ ID NO:1, SEQ ID NO:2, SEQ ID NO:3, SEQ ID NO:4, and SEQ ID NO:5, with a fluorophore conjugated to the peptide. Preferably, the peptide is no more than 50 amino acids in length. The fluorophore is preferably selected from the group consisting of 5-carboxyfluorescein and 6-carboxyfluorescein and is preferably conjugated, i.e., covalently bonded, to the N-terminal amino acid of the peptide, though other fluorophores and other binding sites could be used. The most preferred fluorophore is 6-carboxyfluorescein, and the most preferred peptide consists of the amino acid sequence of SEQ ID NO:1. Thus, the synthetic fluorescent antigen probe ideally comprises the R51-6CF probe described herein.

The buffer solution provided in the kit is preferably substantially free of sodium chloride because, as described herein, this has been found to produce the best results. Preferably, the buffer solution is a sodium phosphate solution with a concentration in the range of about 20 millimolar to about 50 millimolar, to provide a pH in the range of 6.8 to 7.0.

The diagnostic assay kit is intended to be used in the following way, as should be described in the instructions for use. A serum specimen suspected of containing antibodies to EIAV is diluted with a quantity of the buffer solution provided in the kit to provide a buffered specimen. A dilution of about 1:100 is preferred. Next, enough of the synthetic antigen probe is added to the buffered specimen to yield a probe concentration of about 2 nM. The buffered specimen with added probe is then incubated for a time sufficient to permit binding in solution of EIAV antibodies with the antigen probe to provide a reaction product. An incubation time of about 20 minutes is typically sufficient. The fluorescence polarization of the reaction product is then compared to a blank control, i.e., compared to a buffered solution of the synthetic antigen probe at about the same concentration without added serum.

What is claimed is:

1. A synthetic fluorescent antigen probe comprising:

a peptide comprising a sequence of amino acids selected from the group consisting of SEQ ID NO:1, SEQ ID NO:2, SEQ ID NO:3, SEQ ID NO:4, and SEQ ID NO:5, said sequence of amino acids being in a cyclized form; and a fluorophore conjugated to said peptide, wherein said synthetic fluorescent antigen probe binds to serum antibodies to field strains of equine infectious anemia virus to produce a detectable change in fluorescence polarization.

2. The synthetic fluorescent antigen probe of claim 1, wherein said peptide is 9 to 50 amino acids in length.

3. The synthetic fluorescent antigen probe of claim 2, wherein said fluorophore is selected from the group consisting of 5-carboxyfluorescein and 6-carboxyfluorescein.

4. The synthetic fluorescent antigen probe of claim 3, wherein said fluorophore is 6-carboxyfluorescein.

5. The synthetic fluorescent antigen probe of claim 4, wherein said peptide consists of the amino acid sequence of SEQ ID NO:1.

6. An assay for serum antibodies reactive with an antigen common to a number of field strains of equine infectious anemia virus comprising the steps of:

diluting a serum specimen suspected of containing antibodies reactive with an antigen of equine infectious anemia virus with a buffer solution, to provide a buffered specimen;

adding to said buffered specimen a synthetic fluorescent antigen probe comprising a fluorophore conjugated to a peptide comprising a sequence of amino acids selected from the group consisting of SEQ ID NO:1, SEQ ID NO:2, SEQ ID NO:3, SEQ ID NO:4 and SEQ. ID NO:5, said sequence of amino acids being in a cyclized form;

incubating for a time sufficient to permit binding in solution of said antibodies to said antigen probe to provide a reaction product; and comparing the fluorescence polarization of said reaction product to a blank control as an indication of the presence of said antibodies in said serum specimen.

7. The assay of claim 6, wherein said peptide is 9 to 50 amino acids in length.

8. The assay of claim 7, wherein said fluorophore is selected from the group consisting of 5-carboxyfluorescein and 6-carboxyfluorescein.

9. The assay of claim 8, wherein said fluorophore is 6-carboxyfluorescein.

10. The assay of claim 9, wherein said peptide consists of the amino acid sequence of SEQ ID NO:1.

11. The assay of claim 6, wherein said buffer solution is substantially free of sodium chloride.

12. The assay of claim 11, wherein said buffer solution has a pH in the range of 6.8 to 7.0.

13. The assay of claim 12, wherein said buffer solution contains sodium phosphate in a concentration in the range of about 20 millimolar to about 50 millimolar.

14. A diagnostic assay kit for detecting serum antibodies to a number of field strains of equine infectious anemia virus comprising a synthetic fluorescent antigen probe in an amount suitable for at least one assay and suitable packaging, said synthetic fluorescent antigen probe comprising a fluorophore conjugated to a peptide comprising a sequence of amino acids selected from the group consisting of SEQ ID NO:1, SEQ ID NO:2, SEQ ID NO:3, SEQ ID NO:4, and SEQ ID NO:5, said sequence of amino acids being in a cyclized form, said synthetic fluorescent antigen probe being able to bind with said serum antibodies to produce a detectable change in fluorescence polarization.

15. The kit of claim 14, wherein said peptide is 9 to 50 amino acids in length.

16. The kit of claim 15, wherein said fluorophore is selected from the group consisting of 5-carboxyfluorescein and 6-carboxyfluorescein.

17. The kit of claim 16, wherein said fluorophore is 6-carboxyfluorescein.

18. The kit of claim 17, wherein said peptide consists of the amino acid sequence of SEQ ID NO;1.

19. The kit of claim 14, further comprising a buffer solution.

20. The kit of claim 19, wherein said buffer solution is substantially free of sodium chloride.

21. The kit of claim 20, wherein said buffer solution has a pH in the range of 6.8 to 7.0.

22. The kit of claim 21, wherein said buffer solution contains sodium phosphate in a concentration in the range of about 20 millimolar to about 50 millimolar.

* * * * *